(12) United States Patent
Yoneda et al.

(10) Patent No.: US 8,829,902 B2
(45) Date of Patent: Sep. 9, 2014

(54) PHASE DIFFERENCE ENHANCED IMAGING METHOD (PADRE), FUNCTIONAL IMAGE CREATING METHOD, PHASE DIFFERENCE ENHANCED IMAGING PROGRAM, PHASE DIFFERENCE ENHANCED IMAGING APPARATUS, FUNCTIONAL IMAGE CREATING APPARATUS, AND MAGNETIC RESONANCE IMAGING (MRI) APPARATUS

(75) Inventors: Tetsuya Yoneda, Kumamoto (JP); Yasuhiro Hiai, Kumamoto (JP)

(73) Assignee: National University Corporation Kumamoto University, Kumamoto (JP)

( * ) Notice: Subject to any disclaimer, the term of this patent is extended or adjusted under 35 U.S.C. 154(b) by 553 days.

(21) Appl. No.: 13/140,750

(22) PCT Filed: Dec. 11, 2009

(86) PCT No.: PCT/JP2009/070763
§ 371 (c)(1), (2), (4) Date: Jul. 21, 2011

(87) PCT Pub. No.: WO2010/073923
PCT Pub. Date: Jul. 1, 2010

(65) Prior Publication Data
US 2011/0304330 A1  Dec. 15, 2011

(30) Foreign Application Priority Data
Dec. 26, 2008 (JP) ................................ 2008-334556

(51) Int. Cl.
*G01V 3/00* (2006.01)
*G01R 33/56* (2006.01)
*G01R 33/48* (2006.01)

(52) U.S. Cl.
CPC ............ *G01R 33/56* (2013.01); *G01R 33/5608* (2013.01); *G01R 33/4806* (2013.01)
USPC .......................................... 324/306; 324/307

(58) Field of Classification Search
USPC .......................... 324/306, 307, 309, 312, 314
See application file for complete search history.

(56) References Cited

U.S. PATENT DOCUMENTS

| 6,703,835 B2 * | 3/2004 | Patch et al. .................... 324/307 |
| 7,227,359 B2 * | 6/2007 | Ma ................................. 324/309 |

(Continued)

FOREIGN PATENT DOCUMENTS

| JP | A-2008-093418 | 4/2008 |
| WO | WO 2009/081786 A1 | 7/2009 |

OTHER PUBLICATIONS

Shen et al., "Reconstruction of SWI for Phased Array Head Coil," *Proc. Intl. Soc. Mag. Reson. Med.*, 2006, vol. 14, p. 2973.

(Continued)

*Primary Examiner* — Louis Arana
(74) *Attorney, Agent, or Firm* — Oliff PLC

(57) ABSTRACT

A functional image creating method and a functional image creating apparatus, each enabling rendering of an activated region, are provided. A phase difference image PDr(x) is created using a complex image σr(x) created from an MR signal in an inactive state and a complex image σ'r(x) obtained by filtering the complex image σr(x). A phase difference image PDa(x) is created using a complex image σa(x) created from an MR signal in an active state and a complex image σ'a(x) obtained by filtering the complex image σa(x). Function signal images diff1(x) and diff2(x) are created using the phase difference images PDr(x) and PDa(x), respectively. A magnitude image Mr(x), a magnitude image Ma(x), a standard image, or a morphological image I(x) is masked with the function signal image diff1(x) or diff2(x), thereby a function image I'(x) with an activated region rendered is created.

22 Claims, 5 Drawing Sheets

(56) References Cited

U.S. PATENT DOCUMENTS

| | | | |
|---|---|---|---|
| 7,298,144 B2 * | 11/2007 | Reeder et al. | 324/307 |
| 7,573,265 B2 * | 8/2009 | Haacke | 324/306 |
| 7,755,355 B2 * | 7/2010 | Polzin | 324/306 |
| 2003/0212322 A1 | 11/2003 | Haacke | |
| 2008/0071167 A1 | 3/2008 | Ikedo et al. | |

OTHER PUBLICATIONS

Santiesteban et al., "Object orientation independence of Susceptibility Weighted Imaging by using a Sigmoid-type phase window," *Proc. Intl. Soc. Mag. Reson. Med.*, 2006, vol. 14, p. 2399.

International Search Report in International Application No. PCT/JP2009/070763; dated Mar. 16, 2000 (with English-language translation).

* cited by examiner

PHASE DIFFERENCE ENHANCED IMAGING METHOD (PADRE), FUNCTIONAL IMAGE CREATING METHOD, PHASE DIFFERENCE ENHANCED IMAGING PROGRAM, PHASE DIFFERENCE ENHANCED IMAGING APPARATUS, FUNCTIONAL IMAGE CREATING APPARATUS, AND MAGNETIC RESONANCE IMAGING (MRI) APPARATUS

TECHNICAL FIELD

The present invention relates to, for enhancement of an objective tissue, a phase difference enhanced imaging method, a phase difference enhanced imaging program, a phase difference enhanced imaging apparatus, and a magnetic resonance imaging apparatus. In addition, the invention relates to a functional image creating method and a functional image creating apparatus for rendering an activated region.

BACKGROUND ART

MRI is a method of imaging internal information of a subject body using a NMR (Nuclear Magnetic Resonance) phenomenon. A complex image having a size and an angle of a rotating magnetization vector is obtained as an MR image. In the past, a magnitude image, obtained by imaging only magnitude of an MR signal, has been used as the MR image. However, since unevenness of a magnetic field has been adequately reduced due to recent progress of MRI technology, a phase image obtained by imaging a rotational angle of a magnetization vector is now available. Along with this, for example, a phase image is used in addition to the magnitude image, so that an SWI (Susceptibility Weighted Imaging) image, enhanced in phase difference by using change in susceptibility, may be provided in practice, as in patent document 1. This has drastically improved image contrast or resolution.

PRIOR ART DOCUMENT

Patent Document

Patent Document 1: U.S. Patent Application Publication No. 2003/0212322

DISCLOSURE OF THE INVENTION

The phase image includes some disturbance in phase of low-frequency component due to unevenness of a magnetic field. In the patent document 1, LPF (Low Pass Filter) is used to remove such phase disturbance. The LPF removes low-frequency component from an original image data using complex quotient and thus works equivalently to HPF (High Pass Filter). In other words, in the patent document 1, size of the LPF is adjusted instead of using HPF and thus the same effect as that of HPF is obtained. Thus, LPF is assumed for discussion of filter size below. Furthermore, in the patent document 1, a phase mask image for enhancing phase difference due to change in susceptibility is created from a filtered phase image. The phase mask image is weighted by some power. The weighted phase mask image corresponds to a polynomial function of phase difference, and the highest degree of which is selected so as to maximize CNR (contrast-to-noise ratios) of an object (for example, a blood vessel) to be desirably enhanced. As the highest degree, a positive number, preferably 4, is typically selected.

In this way, in the method in the patent document 1, a tissue to be desirably provided with contrast is beforehand determined, and a phase mask image is beforehand set so as to enhance a particular phase difference corresponding to the tissue. However, distribution of phase difference is actually changed depending on imaging sites of a subject or imaging conditions. Accordingly, in the case that a polynomial of unified phase difference is used as a phase mask image as in the patent document 1, when an imaging site of a subject or an imaging condition is changed, it is hard to flexibly respond to change in distribution of phase difference even if an exponent is adjusted.

For example, in an actual medical service, imaging may be necessary to be performed with low resolution due to limitation of imaging time, but conversely may be necessary to be performed with high resolution. When resolution needs to be changed in this way, filter size of LPF also needs to be changed depending on resolution levels. This is because gradation is changed more unclearly with increase in filter size. However, since distribution of original phase difference to be enhanced is determined by LPF, when an enhanced image is obtained, if filter size of LPF is changed depending on resolution levels, distribution of phase difference is disadvantageously changed. However, in the patent document 1, since the polynomial of unified phase difference is used as the phase mask image, it is hard to flexibly respond to change in distribution of phase difference by the exponent. Accordingly, for example, the patent document 1 has had the following difficulty: when resolution is changed, contrast is also changed, preventing secure enhancement of an objective tissue.

The present invention is made to solve the above-described issue, and it is a first object to provide a phase difference enhanced imaging method, a phase difference enhanced imaging program, a phase difference enhanced imaging apparatus, and a magnetic resonance imaging apparatus, which enable secure enhancement of an objective tissue even if an imaging site or an imaging condition is changed. In addition, it is a second object to provide a functional image creating method and a functional image creating apparatus, enabling rendering of an activated region using the phase difference enhanced imaging method.

A phase difference enhanced imaging method according to the invention includes the following steps (A1) to (A3). A phase difference enhanced imaging program according to the invention allows a computer to execute the following steps (A1) to (A3).

(A1) A first step of creating a phase difference image using a first complex image including a magnitude image and a phase image obtained from a magnetic resonance signal and a second complex image obtained by filtering the first complex image.

(A2) A second step of creating an enhanced image through selecting a phase corresponding to an objective tissue in the phase difference image taking account of change in distribution of phase difference due to filtering, and selecting an exponential function as an enhancement function for enhancing the selected phase, and enhancing the selected phase by the exponential function.

(A3) A third step of creating a phase difference enhanced image by masking a predetermined image with the enhanced image.

A phase difference enhanced imaging apparatus according to the invention includes a phase difference image creation section, an enhanced image creation section, and a phase difference enhanced image creation section. The phase difference image creation section creates a phase difference image using a first complex image including a magnitude image and a phase image obtained from a magnetic resonance signal and a second complex image obtained by filtering the first complex image. The enhanced image creation section creates an enhanced image through selecting a phase corresponding to an objective tissue in the phase difference image taking account of change in distribution of phase difference due to filtering, and selecting an exponential function as an enhancement function for enhancing the selected phase, and enhancing the selected phase by the exponential function. The phase difference enhanced image creation section creates a phase difference enhanced image by masking a predetermined image with the enhanced image.

A magnetic resonance imaging apparatus according to the invention includes a wave detector applying a static magnetic field, a gradient magnetic field, and an RF magnetic field to an object and detecting a magnetic resonance signal emitted from the object, and an image creation section creating an image based on the magnetic resonance signal detected by the wave detector. The image creation section has the same components as those of the phase difference enhanced imaging apparatus.

In the phase difference enhanced imaging method, the phase difference enhanced imaging program, the phase difference enhanced imaging apparatus, and the magnetic resonance imaging apparatus according to the invention, a phase corresponding to an objective tissue in a phase difference image created using a first complex image and a second complex image is selected taking account of change in distribution of phase difference due to filtering. This makes it possible to optionally select a phase corresponding to a tissue to be desirably provided with contrast. In addition, an exponential function is selected as an enhancement function for enhancing the selected phase. This, for example, makes it possible to approximate an optional power function with optional accuracy, enabling flexible response to change in distribution of phase difference.

A first functional image creating method according to the invention includes the following steps (B1) to (B4).

(B1) A first step of creating a third complex image, including a magnitude image and a phase image, from a magnetic resonance signal in an inactive state of an objective tissue, and creating a fourth complex image, including a magnitude image and a phase image, from a magnetic resonance signal in an active state of the objective tissue.

(B2) A second step of creating a fifth complex image by filtering the third complex image and creating a sixth complex image by filtering the fourth complex image, and then creating a first phase difference image using the third complex image and the fifth complex image and creating a second phase difference image using the fourth complex image and the sixth complex image.

(B3) A third step of creating a first function signal image through creating phase difference variation by obtaining a difference between the first and second phase difference images, and then selecting a first exponential function as an enhancement function for enhancing the phase difference variation, and enhancing the phase difference variation by the first exponential function.

(B4) A fourth step of creating a first function image with an activated region rendered by masking a predetermined image with the first function signal image.

A first functional image creating apparatus according to the invention includes a complex image creation section, a phase difference image creation section, a function signal image creation section, and an activated region rendering section. The complex image creation section creates a third complex image, including a magnitude image and a phase image, from a magnetic resonance signal in an inactive state of an objective tissue, and creates a fourth complex image, including a magnitude image and a phase image, from a magnetic resonance signal in an active state of the objective tissue. The phase difference image creation section creates a fifth complex image by filtering the third complex image and creates a sixth complex image by filtering the fourth complex image, and then creates a first phase difference image using the third complex image and the fifth complex image and creates a second phase difference image using the fourth complex image and the sixth complex image. The function signal image creation section creates a first function signal image through creating phase difference variation by obtaining a difference between the first and second phase difference images, and then selecting a first exponential function as an enhancement function for enhancing the phase difference variation, and enhancing the phase difference variation by the first exponential function. The activated region rendering section creates a first function image with an activated region rendered by masking a predetermined image with the first function signal image.

In the first functional image creating method and the first functional image creating apparatus according to the invention, the first function signal image is created by enhancing, by the enhancement function, a difference (phase difference variation) between the first phase difference image in the inactive state created using the third and fifth complex images and the second phase difference image in the active state created using the fourth and sixth complex images. This makes it possible to reflect the BOLD (Blood Oxygen Level Dependent) effect induced by an activated tissue, and besides to distinguish a signal caused by entering of blood flow (for example, a signal due to a two-dimensional effect caused by activation of a tissue in a large blood vessel other than a capillary vessel). In addition, an exponential function is selected as an enhancement function in the invention. This, for example, makes it possible to approximate an optional power function with optional accuracy, enabling flexible response to change in distribution of phase difference.

A second functional image creating method according to the invention includes the following steps (C1) to (C4).

(C1) A first step of creating a third complex image, including a magnitude image and a phase image, from a magnetic resonance signal in an inactive state of an objective tissue, and creating a fourth complex image, including a magnitude image and a phase image, from a magnetic resonance signal in an active state of the objective tissue.

(C2) A second step of creating a fifth complex image by filtering the third complex image and creating a sixth complex image by filtering the fourth complex image, and then creating a first phase difference image using the third complex image and the fifth complex image and creating a second phase difference image using the fourth complex image and the sixth complex image.

(C3) A third step of creating a second function signal image through selecting a second exponential function as an enhancement function for enhancing the first and second phase difference images, creating first and second enhanced images by enhancing the first and second phase difference images by the second exponential function, respectively, and obtaining a difference between the first and second enhanced images.

(C4) A fourth step of creating a second function image with an activated region rendered by masking a predetermined image with the second function signal image.

A second functional image creating apparatus according to the invention includes a complex image creation section, a phase difference image creation section, a function signal image creation section, and an activated region rendering section. The complex image creation section creates a third complex image, including a magnitude image and a phase image, from a magnetic resonance signal in an inactive state of an objective tissue, and creates a fourth complex image, including a magnitude image and a phase image, from a magnetic resonance signal in an active state of the objective tissue. The phase difference image creation section creates a fifth complex image by filtering the third complex image and creates a sixth complex image by filtering the fourth complex image, and then creates a first phase difference image using the third complex image and the fifth complex image and creates a second phase difference image using the fourth complex image and the sixth complex image. The function signal image creation section creates a second function signal image through selecting a second exponential function as an enhancement function for enhancing the first and second phase difference images, creating first and second enhanced images by enhancing the first and second phase difference images by the second exponential function, respectively, and obtaining a difference between the first and second enhanced images. The activated region rendering section creates a second function image with an activated region rendered by masking a predetermined image with the second function signal image.

In the second functional image creating method and the second functional image creating apparatus according to the invention, the second function signal image is created by obtaining a difference between the first and second enhanced images created by enhancing the first phase difference image in the inactive state and the second phase difference image in the active state by the exponential function, respectively. This makes it possible to reflect the BOLD (Blood Oxygen Level Dependent) effect induced by an activated tissue, and besides to distinguish a signal caused by entering of blood flow (for example, a signal due to a two-dimensional effect caused by activation of a tissue in a large blood vessel other than a capillary vessel). In addition, an exponential function is selected as an enhancement function in the invention. This, for example, makes it possible to approximate an optional power•function with optional accuracy, enabling flexible response to change in distribution of phase difference.

According to the phase difference enhanced imaging method, the phase difference enhanced imaging program, the phase difference enhanced imaging apparatus, the magnetic resonance imaging apparatus, the first and second functional image creating methods, and the first and second functional image creating apparatus according to the invention, a phase corresponding to a tissue to be desirably provided with contrast may be optionally selected, and flexible response may be made to change in distribution of phase difference. This enables adjustment of filter size or change of a filter type in correspondence to an objective tissue as well as selection of phase difference, and consequently, even if an imaging site or an imaging condition is changed, the same or similar contrast may be maintained. Accordingly, even if an imaging site or an imaging condition is changed, an objective tissue may be securely enhanced.

Furthermore, the first and second functional image creating methods and the first and second functional image creating apparatus according to the invention make it possible to reflect the BOLD effect induced by an activated tissue, and besides to distinguish a signal caused by entering of blood flow. Furthermore, a function image with high spatial resolution may be created due to phase information sensitive to oxygen metabolism of a tissue or the like. Consequently, an activated region is shown mainly in a cortex portion, allowing accurate display of the activated region even from an anatomical standpoint.

MODE FOR CARRYING OUT THE INVENTION

Hereinafter, modes for carrying out the invention will be described in detail with reference to drawings. Description is made in the following order.
1. First Embodiment
Creation of morphological image by phase difference enhanced imaging method (PADRE)
2. Modification of First Embodiment
Example of RF coil section having multi-channel configuration
3. Second Embodiment
Creation of function image using data in inactive and active states
4. Modification of Each of Embodiments
Creation of function image using LPFs having different kinds of filter size
The morphological image in the above index corresponds to a specific example of "phase difference enhanced image" in the invention.

First Embodiment

Figure 1:
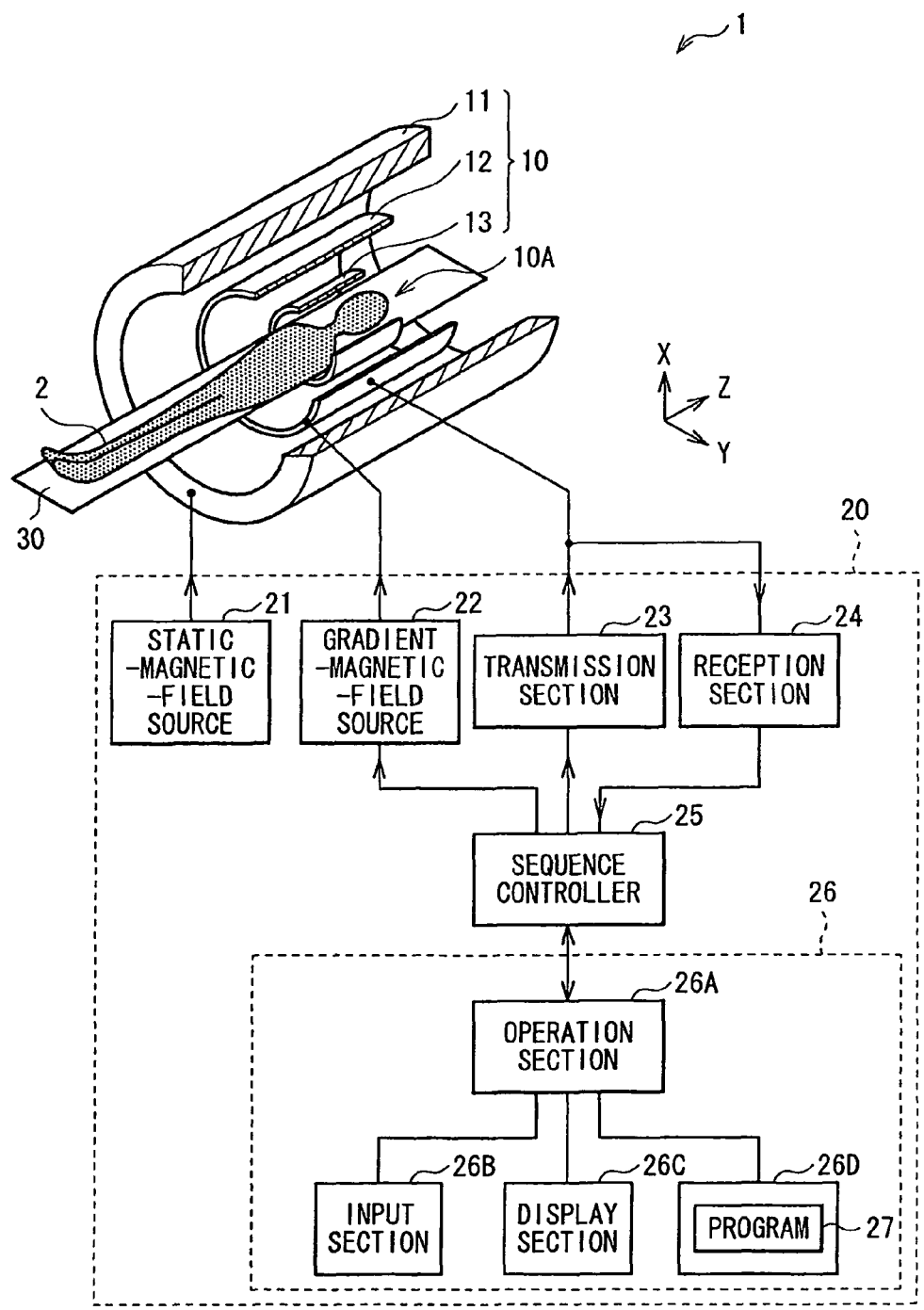
FIG. 1 is a rough configuration diagram of MRI according to a first embodiment of the invention.

FIG. 1 illustrates a schematic configuration of an MRI apparatus 1 (magnetic resonance imaging apparatus) according to a first embodiment of the invention. Since a phase difference enhanced imaging method, a phase difference enhanced imaging program, and a phase difference enhanced imaging apparatus according to an embodiment of the invention are embodied by the MRI apparatus 1, description of them is made in conjunction with description of the MRI apparatus 1 below.

The MRI apparatus 1 performs imaging of internal information of a subject 2 using the NMR phenomenon. The MRI apparatus 1 is a new type of MRI apparatus, which renders a morphological image using a phase image obtained by imaging a rotational angle of a magnetization vector, as well as a magnitude image obtained by imaging magnitude of an MR signal, as described later. The MRI apparatus 1 includes, for example, a coil system 10 and a control system 20 as shown in FIG. 1.

[Coil System 10]
The coil system 10 includes, for example, a static-magnetic-field coil section 11, a gradient-magnetic-field coil section 12, and an RF (Radio Frequency) coil section 13. For example, the coil sections have an approximately cylindrical shape each, and are disposed such that central axes (not shown) thereof are coaxial with one another. A bed section 30 is provided to support the subject 2 in a plane including the central axes. The bed section 30 is placed in a bore 10A (internal space) of the coil system 10. The subject 2 on the bed section 30 is carried into or out of the bore 10A with movement of the bed section 30 using a not-shown carrying device. In the embodiment, a direction parallel to a central axis is a Z-axis direction, and respective, two directions orthogonal to the Z-axis are an X-axis direction and a Y-axis direction as shown in FIG. 1.

The static-magnetic-field coil section 11 forms a static magnetic field in the bore 10A, and is configured of, for example, a superconducting coil or a normal-conducting coil. A direction of the static magnetic field is approximately parallel to the Z-axis direction. While FIG. 1 illustrates a case where a body axis direction of the subject 2 is parallel to the direction of the static magnetic field, the body axis direction may be orthogonal to the direction of the static magnetic field.

For example, the gradient-magnetic-field coil section 12 forms gradient magnetic fields in respective directions of three axes perpendicular to one another, namely, a slice axis, a phase axis, and a frequency axis. The gradient-magnetic-field coil section 12 includes, for example, three types of coils, a coil for a slice axis direction, a coil for a phase axis direction, and a coil for a frequency axis direction. Any of the X-axis, the Y-axis, and the Z-axis may be set as the slice axis. For example, when the Z-axis is set as the slice axis, the X-axis may be set as the phase axis and the Y-axis as the frequency axis. The MR signal may be collected on a coordinate system (for example, polar coordinate system) other than the Cartesian coordinate system assumed in the above. When the MR signal is collected on such a coordinate system, axes suitable for the coordinate system (for example, axes in radial and angular directions) are set.

Figure 2:
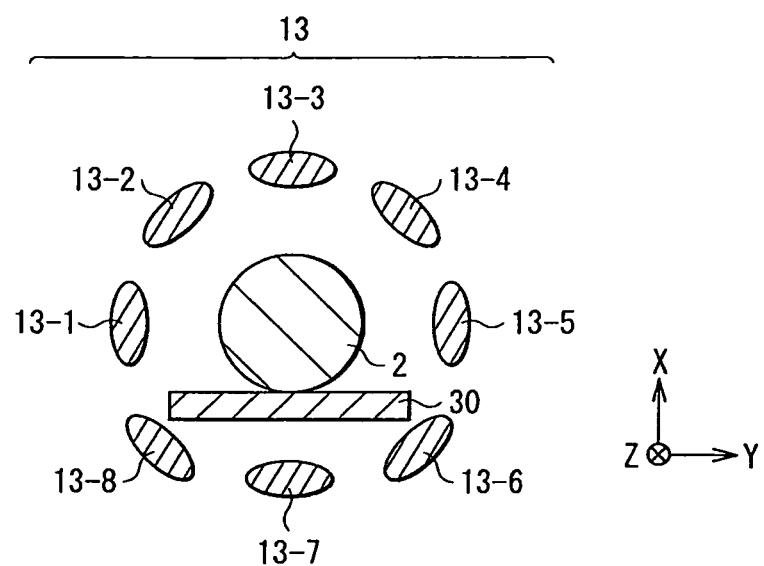
FIG. 2 is a sectional configuration diagram illustrating a modification of an RF coil section in FIG. 1.

The RF coil section 13 forms an RF magnetic field for spin excitation within the subject 2 in a static-magnetic-filed space, and receives an MR signal generated with the excitation caused by the formed RF magnetic field. In the RF coil section 13, a coil for receiving the MR signal may serve even as a coil for forming the RF magnetic field, or may be provided separately from the coil for forming the RF magnetic field. The RF coil section 13 may include a single coil, or, for example, include a plurality of coils 13-1 to 13-8 (multiple channels) as shown in FIG. 2. When the RF coil section 13 includes multiple channels, an MR signal may be provided for each of channels.

The MR signal is obtained by, for example, a GE (gradient echo) pulse sequence, and is a sampling signal in a frequency domain, namely, in a Fourier space (k-space). A GE method includes, for example, steady state in addition to GE. The pulse sequence may be, for example, a Balanced SSFP (Steady State Free Precession) pulse sequence or a True FISP (True Fast Imaging with Steady-state Precession) pulse sequence, or may be a pulse sequence other than the GE pulse sequence such as SE (Spin Echo) pulse sequence.

[Control System 20]

The control system 20 includes, for example, a static-electric-field source 21, a gradient-magnetic-field source 22, and a transmission section 23, which collectively drive the coil system 10; a reception section 24 receiving an MR signal caused by driving of the coil system 10; and a sequence controller 25 controlling the gradient-magnetic-field source 22, the transmission section 23, and the reception section 24, as shown in FIG. 1. The static-electric-field source 21, the gradient-magnetic-field source 22, the transmission section 23, the reception section 24, the sequence controller 25, and the coil system 10 collectively correspond to a specific example of "wave detector" of the invention.

The static-electric-field source 21 supplies power to the static-magnetic-field coil section 11. Power supplied to the static-magnetic-field coil section 11 causes formation of a static magnetic field in the bore 10A. The gradient-magnetic-field source 22 supplies power to the gradient-magnetic-field coil section 12 based on a control signal inputted from the sequence controller 25. Power supplied to the gradient-magnetic-field coil section 12 causes formation of a desired, gradient magnetic field in each of directions of the slice axis, the phase axis, and the frequency axis.

For example, the transmission section 23 applies an RF signal to the RF coil section 13 based on a control signal inputted from the sequence controller 25. For example, the reception section 24 detects the MR signal received by the RF coil section 13, performs necessary signal processing and A/D (Analog-to-Digital) conversion of the signal, and thus generates digitalized complex data (raw data). The reception section 24 may generate the raw data through direct A/D conversion of the detected MR signal. The generated raw data are outputted to, for example, the sequence controller 25.

For example, the sequence controller 25 generates a control signal necessary for driving each of the gradient-magnetic-field source 22, the transmission section 23, and the reception section 24, and applies the generated control signal to each of the sections 22, 23, and 24. For example, the control signal is generated in accordance with a pulse sequence specifying magnitude, application time, and application timing of a pulse current applied to each of the gradient-magnetic-field source 22, the transmission section 23, and the reception section 24. Information of the pulse sequence is inputted to the sequence controller 25 from an information processor 26 described later. In addition, the sequence controller 25 outputs, for example, the raw data received from the reception section 24 to the information processor 26.

The control system 20 further includes, for example, the information processor 26 (phase difference enhanced imaging apparatus) as shown in FIG. 1. The information processor 26 includes, for example, an operation section 26A, an input section 26B, a display section 26C, and a storage section 26D. The operation section 26A corresponds to a specific example of "phase difference image creation section", "enhanced image creation section", "phase difference enhanced image creation section", or "image creation section" of the invention.

For example, the input section 26B is a device that loads information from a user, as digital data, into the information processor 26, and is configured of, for example, a keyboard, a mouse, or a scanner. The display section 26C displays a result (for example, morphological image) processed by the operation section 26A or dialogue for inputting data such as an imaging condition, and is configured of, for example, a display device such as a liquid crystal display device. The storage section 26D storages various programs for controlling the MRI apparatus 1, for example, a program 27 (phase difference enhanced imaging program) used for executing the phase difference enhanced imaging method (PADRE).

For example, the operation section 26A interprets and executes a command in each of the programs, and is configured of, for example, CPU (Central Processing Unit). For example, the operation section 26A is loaded with the program 27 stored in the storage section 26D concurrently with start of the MRI apparatus 1, and thus interprets and executes a command in the program 27, for example, in accordance with a user instruction. The operation section 26A may be configured of hardware corresponding to a function of each of the programs (for example, program 27).

Hereinafter, it is assumed that a morphological image is created through execution of a command in the program 27 by the operation section 26A. In the embodiment, PADRE is used for creating the morphological image. Description of PADRE is inclusively made in the following description of operation of the MRI apparatus 1.

Next, an example of operation of the MRI apparatus 1 of the embodiment is described.

A magnitude image and a phase image are necessary for obtaining the morphological image. While the GE pulse sequence is preferably used for obtaining such images, for example, another pulse sequence in the GE method or a pulse sequence in a method other than the GE method may be used.

The phase image obtained using the GE pulse sequence is proportional to the product (ΔB*TE) of variation ΔB of a local magnetic field (local magnetic field with respect to an external magnetic field) generated by a tissue included in each pixel and echo time (TE) taken for imaging. It is therefore necessary to increase TE or changing a function for enhancing ΔB (so-called enhancement function) to a stronger one in order to extract large phase (difference) information from the phase image. In the embodiment, an enhancement function is selected to be able to flexibly respond to change in imaging parameter such as TE, thereby even if the imaging parameter such as TE or filter size is changed, the same enhanced image (described later) is typically obtained.

[Phase Difference Enhanced Imaging Method (PADRE)]

Hereinafter, PADRE is described in detail. PADRE is a method where a portion of an obtained phase difference image PD(x) (described later) is optionally selected, and part or all of the portion is chosen and enhanced using an enhancement function w(θ) (described later), and therefore a portion of the image corresponding to selected phase information is expressed on a magnitude image M(x) (described later). Furthermore, PADRE refers to presenting the image obtained using the enhancement function w(θ). In PADRE, a predetermined pulse sequence is used for imaging. The number of times of imaging may be one, or may be two or more to allow use of statistics. When the RF coil section 13 includes multiple channels, and an MR signal is obtained for each of the channels, a morphological image may be created by, for example, the following two methods.

The first is a method where an arithmetic mean of MR signals obtained for respective channels is calculated, and a magnitude image and a phase image are created using the arithmetic mean of MR signals, and then a morphological image is created. The second is a method where magnitude images and phase images are formed for respective channels from MR signals obtained for respective channels, and then morphological images are created for respective channels, then an arithmetic mean of the morphological images for respective channels is calculated, and therefore a morphological image is created. In either method, the magnitude image and the phase image obtained from the MR signal are used in PADRE to create the morphological image. In the former case, sensitivity correction may be beforehand performed for individual MR signals to calculate the arithmetic mean. In the latter case, a weighted mean may be used in place of the arithmetic mean. Specifically, a morphological image may be created through weighting individual morphological images by some factor, and calculating a mean of the weighted morphological images. A process from detection of the MR signal to creation of the morphological image is described in detail below.

(Acquisition of Raw Data R)

Figure 3:
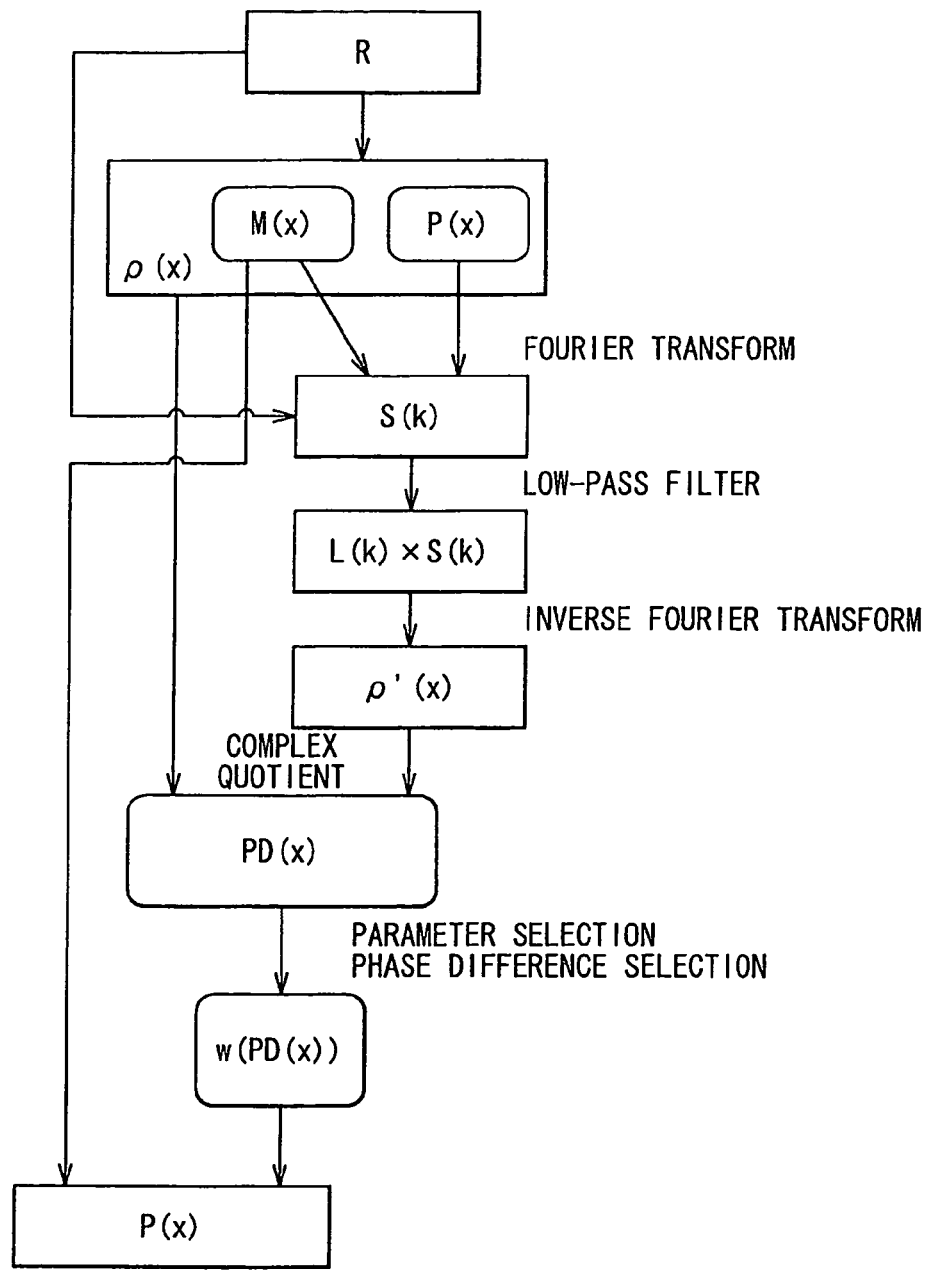
FIG. 3 is a flowchart illustrating data flow through creation of a morphological image.

FIG. 3 illustrates data flow through creation of the morphological image. The operation section 26A starts operation in response to an instruction from a user. The operation section 26A first outputs a control signal requesting the sequence controller 25 to acquire raw data using a predetermined pulse sequence. Thus, the sequence controller 25 outputs a control signal in accordance with the predetermined pulse sequence to each of the gradient-magnetic-field source 22, the transmission section 23, and the reception section 24. Each of the gradient-magnetic-field source 22 and the transmission section 23 outputs a predetermined current pulse to the coil system 10 in response to the outputted control signal, and the RF coil section 13 detects an MR signal. The detected MR signal is converted into raw data R through predetermined signal processing by the reception section 24. The obtained raw data R are inputted from the reception section 24 to the sequence controller 25, and then the controller 25 transfers (inputs) the raw data to the operation section 26A. In this way, the operation section 26A acquires data (raw data R) corresponding to the MR signal.

(Creation of Magnitude Image M(x) and Phase Image P(x))

Next, the operation section 26A disposes the raw data R inputted from the sequence controller 25 in a k space set in an internal memory (not shown). Data disposed in the k space are called k-space data S(k). The operation section 26A performs inverse Fourier transform of the k-space data S(k) disposed in the k space to reconstruct an image. Such reconstruction provides a complex image ρ(x) (first complex image) having a real image in a real part and an imaginary image in an imaginary part. The operation section 26A obtains a magnitude image M(x) and a phase image P(x) from the complex image ρ(x).

(Creation of Phase Difference Image PD(x))

In the embodiment, long TE is used for acquiring the MR signal. This causes phase wrapping in the phase image P(x), so that a phase of more than 2π has a phase value corresponding to actual phase minus 2πn (n is an integer). As a result, the phase image P(x) becomes a striped-pattern image, and thus loses an original phase value. Thus, the operation section 26A performs processing to extract phase difference while removing the phase wrapping.

Specifically, the operation section 26A first performs Fourier transform of the complex image ρ(x) to temporarily return the complex image ρ(x) to the k-space data S(k). Alternatively, the operation section 26A reads the k-space data S(k) that have been disposed in the k space. Next, the operation section 26A filters the S(k) with LPF (Low Pass Filter) and performs inverse Fourier transform of data L(k)*S(k) obtained thereby, and thus obtains a complex image ρ'(x) (second complex image). The L(k) denotes a function of LPF.

Next, the operation section 26A creates a phase difference image PD(x) using the complex image ρ(x) and the complex image ρ'(x). Specifically, the operation section 26A divides the complex image ρ(x) by the complex image ρ'(x) as operation of a complex quotient, and thus creates the phase difference image PD(x). This allows phase wrapping in a phase part to be removed. Here, phase difference included in the phase difference image PD(x) has a width of 2π. In the embodiment, the phase difference in the phase difference image PD(x) is assumed to be $-\pi \leq PD(x) < \pi$. A sign of phase difference in the phase difference image PD(x) is determined by $-\gamma*\Delta B*TE$. However, even if a level of phase difference is unchanged, the sign of phase difference in the phase difference image PD(x) may be changed by changing definition of LPF and definition of the complex quotient in extraction of the phase difference image PD(x). To cope with this, the definitions are made such that the sign is negative particularly for venous blood. The γ is a positive constant of proportion, and corresponds to, for example, a gyromagnetic ratio of hydrogen.

(Creation of Enhanced Image w(PD(x)))

Next, the operation section 26A optionally selects a phase θ as a part of the phase difference image PD(x), and enhances the selected phase θ. Specifically, the operation section 26A first selects a phase θ corresponding to an objective tissue in the phase difference image PD(x) taking account of change in distribution of phase difference due to filtering.

Figure 4:
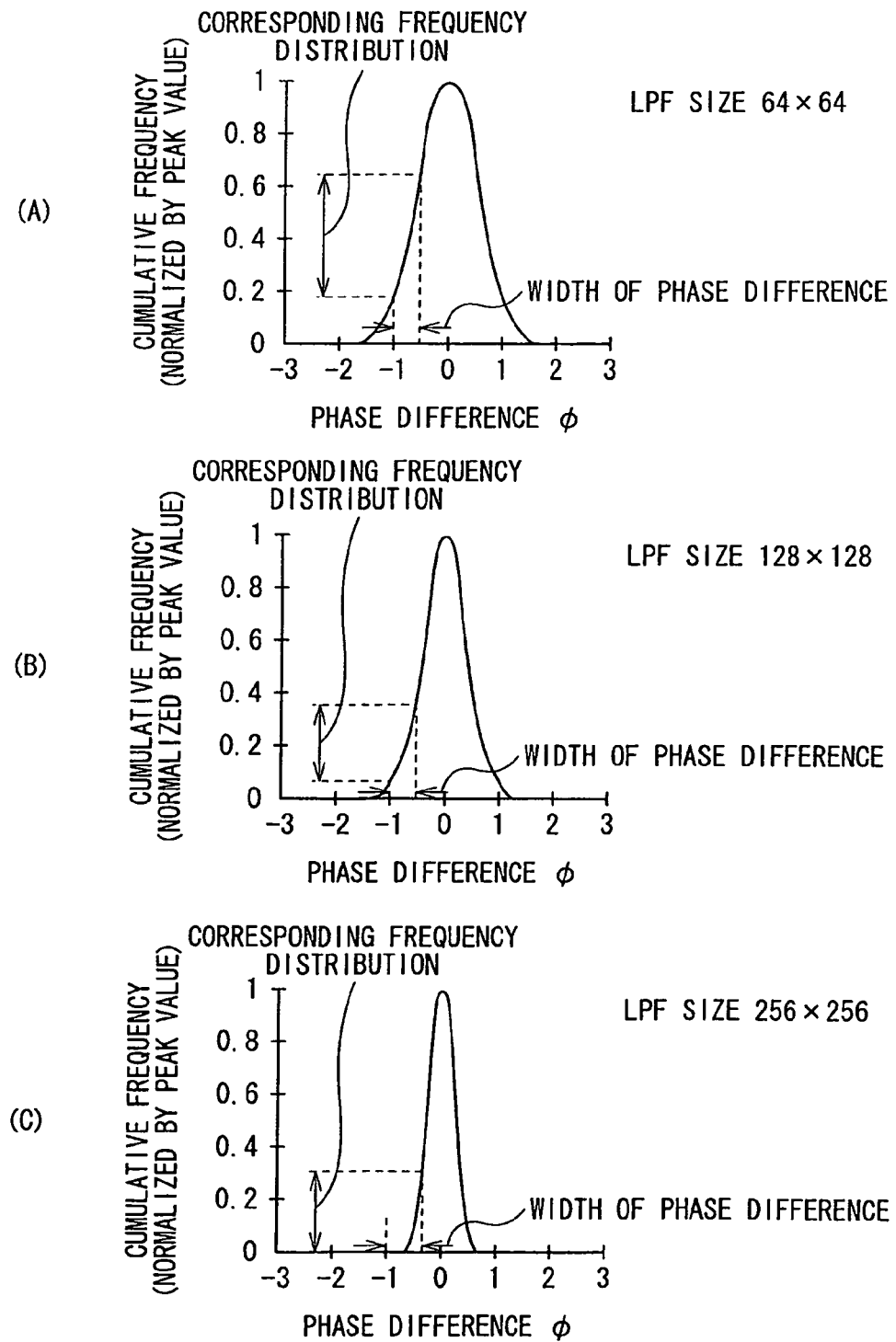
FIG. 4 is a schematic diagram for explaining a relationship between distribution of phase difference and LPF size.

The distribution of phase difference is changed, for example, as in a model shown in FIGS. 4(A) to 4(C), for example, due to change of LPF size. In other words, width of distribution of phase difference, which is approximately symmetric about phase difference zero, decreases with increase in LPF size. Consequently, the phase difference image mainly has values of phase difference, zero and near zero, and therefore a tissue is hardly provided with contrast in the phase difference image. On the other hand, for a tissue having a fine structure, contrast is more easily provided in the case of using LPF larger in size compared with the case of using LPF smaller in size. Such a phenomenon may be simply understood considering that the complex quotient used for obtaining the phase difference image corresponds to exponential subtraction. In other words, in exp(ϕ-ϕ') (ϕ: all phases including phase wrapping, ϕ': phase of low-pass component (low-frequency component) mainly including phase wrapping), when LPF size corresponds to full-image size, since such a case means that all frequencies are included, ϕ=ϕ' holds true and phase difference becomes close to zero. Width of distribution of phase difference is therefore increasingly reduced.

However, this is merely extreme tendency, and it is virtually difficult to predict a distribution type in the case of using a particular filter in a normal tissue. To respond to such change in distribution of phase difference, the embodiment is designed such that a flexibly responsive function is selected as an enhancement function described later so that the same contrast may be provided to images having different frequency distribution patterns against the same phase difference as shown in FIGS. 4(A) to 4(C).

For example, the operation section 26A selects width of phase difference and a central value thereof such that contrast of an objective tissue has a desired level. Selection of the width of phase difference and the central value thereof may be left to a user of the MRI apparatus 1 instead of the operation section 26A. In such a case, the operation section 26A selects a phase θ of an objective tissue taking account of change in distribution of phase difference due to filtering.

Next, the operation section 26A enhances the selected phase θ using an enhancement function w(θ) and thus obtains an enhanced image w(PD(x)).

Here, an exponential function is used as the enhancement function w(θ). In the embodiment, a π function is used as an example of the exponential function. The π function is expressed by the following two expressions.

$$w(\theta)=1 \ldots (-\sigma \le \theta \le \sigma)$$

$$w(\theta)=\exp(-a^*(Abs(\theta)-\sigma)^b) \ldots (\theta \text{ is out of the above rage})$$

(Determination of a, b, and σ)

Any of parameters a, b, and σ has a value of a real number. The respective parameters a and b adjust a level of phase difference enhancement, and are determined depending on filter size of LPF. Furthermore, the respective parameters a and b are determined to maximize contrast C between an objective tissue and a background thereof or a contrast-to-noise ratio CNR. The parameter σ reduces noise on the phase difference image PD(x), and is determined, for example, by a standard deviation of tissues each having a mean phase value of approximately 0 (zero) on the phase difference image PD(x). The parameter σ may be obtained based on data obtained through many experiments. However, in some cases, any of tissues on any of phase difference images PD(x) captured at the same time does not have a mean phase value of approximately 0 (zero). In such a case, the parameter σ is determined, for example, based on the contrast C or the contrast-to-noise ratio CNR.

The contrast C is determined by a difference, expressed by an absolute value, between a signal w(PD(x1))*M(x1) of an enhanced objective tissue on a position x1 on an image and a signal w(PD(x2))*M(x2) of a background of an enhanced tissue on a position x2 on the image, as expressed by an expression below. The contrast-to-noise ratio CNR is expressed by C/σ' as in the following expression. The σ' is determined by a standard deviation on an enhanced image of an objective tissue or a standard deviation on an enhanced image of a background of an objective tissue. However, any of the standard deviations is not usable for determining σ' in some cases. In such a case, a standard deviation of external signals of the subject 2 or a standard deviation using a finite difference method is used. A π function specified by σ determined in this way is used, thereby only a noise portion of phase difference may be removed, and consequently a PADRE image having a high S/N ratio may be created. Such an advantage is unique, or not provided in the mask (negative phase mask) in the patent document 1.

$$C\text{Abs}(w(PD(x1))^*M(x1)-w(PD(x2))^*M(x2))$$

$$CNR=C/\sigma'$$

Abs(θ) denotes an absolute value of θ. The π function enhances the phase difference image PD(x) in any range other than a range of Abs(θ)≤σ. The π function may approximate an optional power function with optional accuracy, which makes it possible to perform more flexible enhancement compared with a case that a polynomial is used as an enhancement function.

For example, when filter size of LPF is changed in accordance with size of an imaging region, distribution of phase difference is accordingly changed slightly. In contrast, when filter size of LPF is changed while size of the imaging region is fixed, distribution of phase difference is accordingly changed significantly. In this way, when imaging conditions or the like are different from each other, distributions of phase difference are also different from each other. Accordingly, when the same enhancement function is typically used regardless of imaging conditions, respective contrasts are changed, and consequently an objective tissue may not be securely enhanced. On the other hand, in the embodiment, the respective parameters a, b, and σ have values of real numbers, which may be flexibly changed depending on imaging conditions. This makes it possible to maintain the same or similar contrast even if an imaging condition is changed.

Here, description is made on a relationship between the parameter a or b and a parameter q in the mask (negative phase mask) described in the patent document 1. Since the right side of the second expression of the two expressions is equal to $[\exp(-(Abs(\theta)-\sigma)^b)]^a$, the parameter a has quite the same meaning as that of the parameter q. However, when the parameter b has a particular value of 2, the π function comes down to a Gaussian function. In such a case, it is believed that since the parameter a is proportional to a reciprocal of dispersion, the parameter has a function of adjusting a spread of the enhancement function. In addition, it is believed that when Abs(θ) has a value away from 0 (zero), the parameter b has a function to adjust a degree of enhancement depending on a distance from 0 (zero).

On the other hand, the mask described in the patent document 1 may be expanded as follows.

$$\left(1 - \frac{|\theta|}{\pi}\right)^P = 1 - \sum_{k=1}^{P} {}_PC_k\left(-\frac{|\theta|}{\pi}\right)^{P-k} \quad \text{[Numerical Expression 1]}$$

Here, the second term of the right side of the expression may be set in correspondence to the second term of the right side of an expression obtained by expanding the π function in the same way as above.

$$e^{-a(|\theta|-\sigma)^b} = 1 + \sum_{k=1}^{\infty} \frac{\{-a(|\theta|-\sigma)^b\}^k}{k!} \quad \text{[Numerical Expression 2]}$$

Comparing the two expressions, the parameter b is corresponding to the parameter p. These suggest that an effect of the parameter p is complicatedly incorporated in the π function by the parameters a and b. In other words, the parameters a and b may not be expressed only by the parameter p on the mask described in the patent document 1, meaning that the π function is extremely usable.

(Creation of Morphological Image I(x))

Next, for example, the operation section 26A masks the magnitude image M(x) with the enhanced image w(PD(x)) in accordance with a predetermined mode (rule) and thus obtains the morphological image I(x). A specific condition in masking the magnitude image M(x) with the enhanced image w(PD(x)) may be set depending on an object to be desirably enhanced, and is set basically in correspondence to each of four kinds of enhancement modes (tissue enhancement, blood vessel enhancement, overall enhancement, and structure enhancement). For example, either of the tissue enhancement and the blood vessel enhancement may be selected depending on whether both the parameter σ and the phase difference image PD(x) are positive or negative. The overall enhancement has no dependence on a sign of each of the parameter σ and the phase difference image PD(x). For the structure enhancement, for example, a value of phase difference α caused by a cortical structure (hereinafter, simply called phase difference α) is beforehand experimentally obtained, and a conditional equation is set depending on a relationship in size between the phase difference α and the phase difference image PD(x).

Enhancement Mode A (Tissue Enhancement)

$I(x)=w(PD(x))*M(x) \ldots (PD(x)≥0)$ $I(x)=M(x) \ldots (PD(x)<0)$

Enhancement Mode B (Blood Vessel Enhancement)

$I(x)=w(PD(x))*M(x) \ldots (PD(x)≤0)$ $I(x)=M(x) \ldots (PD(x)>0)$

Enhancement Mode C (Overall Enhancement)

$I(x)=w(PD(x))*M(x)$

Enhancement Mode D (Structure Enhancement)

$|α|≤σ$

In $PD(x)≤0$ $I(x)=w(PD(x))*M(x) \ldots (-|α|≤PD(x)≤-σ)$ $I(x)=M(x) \ldots (PD(x)<-|α|)$ In $PD(x)>0$ $I(x)=w(PD(x))*M(x)$ In the enhancement mode A, the operation section 26A extracts a portion where the phase difference image PD(x) is 0 (zero) or more and enhances only the portion, and thus creates a morphological image I(x). Here, the operation section 26A does not enhance a portion where the phase difference image PD(x) is negative. In the enhancement mode A, the morphological image I(x) corresponds to a tissue-enhanced image.

In the enhancement mode B, the operation section 26A extracts a portion where the phase difference image PD(x) is 0 (zero) or less and enhances only the portion, and thus creates a morphological image I(x). Here, the operation section 26A does not enhance a portion where the phase difference image PD(x) is positive. In the enhancement mode B, the morphological image I(x) corresponds to a blood-vessel-enhanced image.

In the enhancement mode C, the operation section 26A enhances the phase difference image PD(x) as a whole, and thus creates a morphological image I(x). In the enhancement mode C, the morphological image I(x) corresponds to an image enhanced in the whole body including tissues and blood vessels.

In the enhancement mode D, when the phase difference image PD(x) is 0 (zero) or less, the operation section 26A enhances a portion satisfying $-|α|≤PD(x)≤-σ$, and thus creates a morphological image I(x). Here, the operation section 26A does not enhance a portion satisfying $PD(x)<-|α|$. In addition, when the phase difference image PD(x) is 0 (zero) or more, the operation section 26A also creates a morphological image I(x) using the above conditional equations. In the enhancement mode D, the morphological image I(x) corresponds to a structure-enhanced image. Since the phase difference α is caused by a cortical structure, the morphological image I(x) is actually a cortical-structure-enhanced image.

In this way, in the embodiment, a masking way of the magnitude image M(x) with the enhanced image w(PDr(x)) or w(PDa(x)) is changed, and therefore a more accurate anatomical position of a brain function may be specified with tissue contrast shown by each morphological image I(x) as a background.

Next, effects and advantages of the MRI apparatus 1 of the embodiment are described.

In the embodiment, a complex image ρ(x) is obtained from an MR signal, and a magnitude image M(x) and a phase image P(x) are obtained from the complex image ρ(x). The magnitude image M(x) and the phase image P(x) are filtered with LPF in a k space, and thus a filtered complex image ρ'(x) is obtained. The complex image ρ(x) is divided by the filtered complex image ρ'(x), and thus a phase difference image PD(x) is created.

A phase θ corresponding to an objective tissue in the phase difference image PD(x) is selected taking account of change in distribution of phase difference due to filtering, and an exponential function is selected as an enhancement function w(θ) for enhancing the selected phase θ. For example, a π function is used as the exponential function, and a portion corresponding to the exponent of the function includes two parameters a and b for adjusting a level of phase difference enhancement and one parameter σ for reducing noise on the phase difference image PD(x). The parameters a and b are each determined, for example, by filter size and contrast C or a contrast-to-noise ratio CNR, and the parameter σ is determined, for example, based on the phase difference image PD(x). The magnitude image M(x) is masked with the enhanced image w(PD(x)) created through such a determination process, for example, in accordance with a predetermined enhancement mode. Consequently, a morphological image I(x) is created.

To summarize, in the embodiment, a phase difference image PD(x) is created using a complex image ρ(x) including a magnitude image M(x) and a phase image P(x) obtained from an MR signal, and a complex image ρ'(x) obtained by filtering the complex image ρ(x) in a k space. A phase θ corresponding to an objective tissue in the phase difference image PD(x) is selected taking account of change in distribution of phase difference due to filtering, and an exponential function is selected as an enhancement function w(θ) for enhancing the selected phase θ. The parameters included in the exponential function are determined based on an imaging site or an imaging condition. A magnitude image M(x) is masked with an enhanced image w(PD(x)) created through such a determination process, for example, in accordance with a predetermined enhancement mode. Consequently, a morphological image I(x) is created.

(Comparison with Patent Document 1)

In the patent document 1, a tissue to be desirably provided with contrast is beforehand determined, and a phase mask image is beforehand set such that a particular phase difference corresponding to the tissue is enhanced. A user has therefore not been able to provide contrast to a tissue other than the tissue specified by the phase mask image even if the user desires to provide contrast thereto. In contrast, in the embodiment, a particular phase θ corresponding to a tissue to be desirably provided with contrast may be optionally selected in determination of the enhancement function w(θ). Specifically, a phase θ corresponding to an objective tissue may be selected taking account of change in distribution of phase difference due to filtering. This makes it possible to provide contrast to various tissues.

In addition, in the patent document 1, a polynomial of unified phase difference is used as a function of a phase mask image. It is therefore hard to flexibly respond, using an exponent, to change in distribution of phase difference. Accordingly, for example, when resolution needs to be changed, if filter size of LPF is changed depending on resolution levels, contrast is also changed, and consequently an objective tissue has been hard to be securely enhanced. In contrast, in the embodiment, an exponential function, which may approximate an optional power function with optional accuracy, is selected as the enhancement function w(θ), and parameters in the exponential function are determined based on an imaging site or an imaging condition, allowing flexible response to change in distribution of phase difference. This enables adjustment of filter size or change of a filter type in correspondence to an objective tissue as well as selection of phase difference, and consequently, even if an imaging site or an imaging condition is changed, the same or similar contrast may be maintained. As a result, many clinical applications may be proposed compared with a case of the patent document 1.

In the patent document 1, a microvessel having a size of 1 pixel or less may be visualized using high sensitivity of a phase to tissue magnetization. However, a signal caused by a microstructure needs to be distinguished from noise in order to perform that. Noise is generally believed to be randomly generated around the mean value. However, when a subject includes a living body, in which a diamagnetic substance and a paramagnetic substance are partially mixed, this is not necessarily true. However, no measure is taken against such a point in the patent document 1. This is because as long as a polynomial is used as a function of a phase mask image, a measure is extremely hardly taken against noise. In contrast, in the embodiment, an exponential function is selected as the enhancement function w(θ), and, for example, a parameter σ for reducing noise on the phase difference image PD(x) is prepared as a parameter of the exponential function. Accordingly, phase difference selection may be designed in such a manner that a noise portion is beforehand specified, and the specified noise portion is set to be prevented from being enhanced as one of selected phase differences. In this way, phase difference selection is combined with noise removal, and therefore a signal and noise in a pixel may be securely separated from each other. The noise is influenced by filter size. Even in the light of this, an exponential function, which may flexibly enhance the phase in correspondence to filter size, is significantly used as the enhancement function w(θ).

The MRI apparatus 1 of the embodiment may visualize a cortical structure, which has been believed to be difficult for 3TMRI so far. This may be achieved by distinguishing cortexes from white matter by using phase difference, and removing noise in the cortexes, and then enhancing and visualizing a signal caused by the cortical structure. This allows accurate detection of a disease such as cortical dysplasia. Such an advantage is noticed even clinically.

Modification of First Embodiment

In the embodiment, when the RF coil section 13 includes, for example, a plurality of coils 13-1 to 13-8 (multiple channels) disposed on circumference about a central axis (not shown) of the subject 2 as shown in FIG. 2, while a single enhancement function w(θ) may be set, an enhancement function w(θ) is preferably set for each of channels in some cases.

For example, when the enhancement function w(θ) is set for each of channels, for example, the operation section 26A creates a morphological image $I_{indiv}(x)$ in the following way. First, the operation section 26A acquires data (raw data $R_i$) (1≤i≤N: N is total number of channels) from a plurality of channels disposed in parallel around the subject 2, the data being corresponding to an MR signal detected for each of the channels. Next, the operation section 26A creates a magnitude image $M_i(x)$, a phase image $P_i(x)$, and a complex image $\rho_i(x)$ for each of the channels based on the raw data Ri, and then creates a complex image $\rho'_i(x)$ and a phase difference image $PD_i(x)$ for each of the channels. Next, the operation section 26A optionally selects a phase θ as a part of the phase difference image $PD_i(x)$, and enhances the selected phase θ. Specifically, the operation section 26A first selects a phase θ corresponding to an objective tissue in the phase difference image $PD_i(x)$ taking account of change in distribution of phase difference due to filtering. Next, the operation section 26A enhances the selected phase θ with an enhancement function $w_i(\theta)$, thereby obtaining an enhanced image $w_i(PD_i(x))$ for each of the channels. Here, an exponential function is used as the enhancement function $w_i(\theta)$ corresponding to the phase difference image $PD_i(x)$ for each of the channels. Even in the modification, a π function is used as an example of the exponential function. Next, the operation section 26A masks the magnitude image $M_i(x)$ for each of the channels with the enhanced image $w_i(PD_i(x))$ for each of the channels in accordance with a predetermined mode (rule) and thus obtains a morphological image $I_i(x)$ for each of the channels. Next, the operation section 26A obtains an arithmetic mean or a weighted mean of the morphological images $I_i(x)$ for the respective channels (creates the morphological image $I_{indiv}(x)$). In this way, the morphological image $I_{indiv}(x)$ is created.

In the following, description is made on a case where the enhancement function $w(\theta)$ is set for each of channels by comparison with a case where a single enhancement function $w(\theta)$ is set. While a case of using an arithmetic mean is exemplified below, even if a weighted mean is used in place of the arithmetic mean, the same conclusion as in the case of using the arithmetic mean may be obtained. When a morphological image obtained through setting the enhancement function $w(\theta)$ for each of the channels is $I_{indiv}(x)$, and a morphological image obtained through setting the single enhancement function $w(\theta)$ is $I_{av}(x)$, $I_{indiv}(x)$ and $I_{av}(x)$ are obtained from the following numerical expressions 3 and 4, respectively, and difference $\Delta I$ between $I_{indiv}(x)$ and $I_{av}(x)$ is obtained from the following numerical expression 5.

$$I_{indiv}(x) = \frac{1}{N} \sum_i \{W_i(PD_i(x)) \times M_i(x)\} \quad \text{[Numerical Expression 3]}$$

$$I_{av}(x) = W(PD_{av}(x)) \times M_{av}(x) \quad \text{[Numerical Expression 4]}$$
$$= W(PD_{av}(x)) \times \frac{1}{N} \sum_i M_i(x)$$

$$\Delta I = I_{indiv}(x) - I_{av}(x) \quad \text{[Numerical Expression 5]}$$
$$= \frac{1}{N} \sum_i [\{W_i(PD_i(x)) - W(PD_{av}(x))\} M_i(x)]$$

$PD_i(x)$: phase difference image obtained using an MR signal obtained for each of channels $w_i(\theta)$: enhancement function corresponding to a phase difference image $PD_i(x)$ for each of channels $M_i(x)$: magnitude image obtained using an MR signal obtained for each of channels $PD_{av}(x)$: phase difference image obtained using respective arithmetic means of magnitude images and phase difference images obtained for respective channels $w(\theta)$: enhancement function corresponding to an averaged phase difference image $PD_{av}(x)$ $M_{av}(x)$: arithmetic mean of magnitude images obtained for respective channels When the enhancement function $w_i(\theta)$ is assumed to be equal to the enhancement function $w(\theta)$, the enhanced image $w_i(PD_i(x))$ is typically not equal to the enhanced image $w(PD_{av}(x))$. Thus, as known from the numerical expression 5, when the enhancement function $w_i(\theta)$ is equal to the enhancement function $w(\theta)$, $\Delta I$ is typically not zero. In addition, when the enhancement function $w_i(\theta)$ is different from the enhancement function $w(\theta)$, $\Delta I$ is typically not zero. In other words, when the enhancement function $w_i(\theta)$ is set for each of channels, new contrast, different from that in the case of setting the single enhancement function $w(\theta)$, may be made, so that difference in tissue, which has hardly been observed, may be visualized.

A tissue near each channel extremely sensitively responds to a static magnetic field, and accordingly a phase also sensitively responds thereto. This makes it possible to achieve contrast of a small tissue in a phase difference image $PD_i(x)$ before averaging compared with in a morphological image $I_{av}(x)$ created from an averaged phase difference image $PD_i(x)$.

Second Embodiment

Next, an MRI apparatus according to a second embodiment of the invention is described. The MRI apparatus of the embodiment performs imaging of internal information of a subject 2 using an NMR phenomenon in the same way as the MRI apparatus 1 of the first embodiment. However, the MRI apparatus of the embodiment is different in configuration from the MRI apparatus 1 of the above embodiment in that the MRI apparatus has a function of fMRI, or a function of rendering an activated region. Thus, hereinafter, features different from the above embodiment are largely described, and description of features in common with the above embodiment is appropriately omitted.

In the embodiment, a storage section 26D storages various programs for controlling the MRI apparatus of the embodiment, for example, a program (functional image creating program) used for creating a function image as part of a program 27. Hereinafter, the function image is created through execution of a command in the program 27 by an operation section 26A. The MRI apparatus of the embodiment may obtain a function image of part of a brain, a brain as a whole, a site other than a brain, or a wide range of sites including a brain. In the embodiment, the operation section 26A corresponds to a specific example of "complex image creation section", "phase difference image creation section", "function signal image creation section", or "activated region rendering section" of the invention. In the embodiment, PADRE is partially used for creating the function images.

Next, an example of operation of the MRI apparatus of the embodiment is described.

[Functional Brain Image]

A functional brain image is described before starting description of operation of the MRI apparatus. The functional brain image refers to an image showing a portion of a brain activated by thinking, behavior, or external stimulus as described before. To create such an image, it is necessary to present how different an image signal value in an activated state is from an image signal value in a normal state (non-activated state). Thus, when a function image with an activated region rendered is created, it is typically necessary to acquire an image in an active state, where activation is performed, but also an image in an inactive state, where activation is not performed. Here, in the embodiment, a phase image obtained by imaging a rotational angle of a magnetization vector is acquired as an MR image as well as a magnitude image obtained by imaging magnitude of an MR signal. Any pulse sequence necessary for phase creation is allowed for creating the phase image. This is because meanings of phases generated by individual pulse sequences are subtly different from one another. Such a difference in physical meaning between phase images depending on imaging methods is to be reflected on an image created using the phase images. PADRE enables such a difference in meaning to be reflected on the image.

To obtain a function image with an activated region rendered, the magnitude image and the phase image are necessary in each of the active and inactive states as described before. While a GE pulse sequence is preferably used for obtaining such images, for example, another pulse sequence in the GE method or a pulse sequence in a method other than the GE method may be used.

The phase image obtained using the GE pulse sequence is proportional to the product ($\Delta B*TE$) of variation $\Delta B$ of a local magnetic field (local magnetic field with respect to an external magnetic field) generated by a tissue included in each pixel and echo time (TE) taken for imaging. It is therefore necessary to increase TE or change a function for enhancing $\Delta B$ (so-called enhancement function) to stronger one in order to extract large phase (difference) information from the phase image. Moreover, in the embodiment, since time series variation of ΔB varying before and after action (ΔB (in the active state)-ΔB (in the inactive state) is intended to be visualized on an image, difference in ΔB needs to be enhanced. Thus, the enhancement function of ΔB is preferably changed to stronger one in the embodiment.

Hereinafter, description is made on a case where imaging is performed using a predetermined pulse sequence in each of the active state and the inactive state of an objective tissue. Here, an imaging site may be narrowed down to a brain site to be activated by action, or may be a brain as a whole. Imaging time is simply lengthened with increase in size of an imaging site. However, it is important to prevent a slice surface from being moved during imaging in both the active and inactive states. This is because if the slice surface is moved, difference in ΔB becomes incorrect. The number of times of imaging may be one in each of the active and inactive states, or may be two or more so as to use statistics.

When the RF coil section 13 includes multiple channels, and an MR signal is obtained for each of the channels, a function signal image (described later) may be created by, for example, the following two methods.

The first is a method where an arithmetic mean of MR signals obtained for respective channels is calculated, and a magnitude image and a phase image are created using the arithmetic mean of MR signals, and then a function signal image is created. The second is a method where a magnitude image and a phase image are created for each of the channels from an MR signal obtained for each of the channels, and then function signal images are created for respective channels, then an arithmetic mean of the function signal images for respective channels is calculated, and therefore a function signal image is created. In either method, the magnitude image and the phase image obtained from the MR signal are used in PADRE to create the function signal image. In the former case, sensitivity correction may be beforehand performed for individual MR signals for calculating the arithmetic mean. In the latter case, a weighted mean corresponding to sensitivity correction may be used in place of the arithmetic mean. Specifically, a function signal image may be created through weighting individual function signal images by some factor, and calculating a mean of the weighted function signal images. A sequential process of detection of the MR signal, creation of the function signal image, and creation of the function image is described in detail below.

(Acquisition of Raw Data Rr or Ra)

Figure 5:
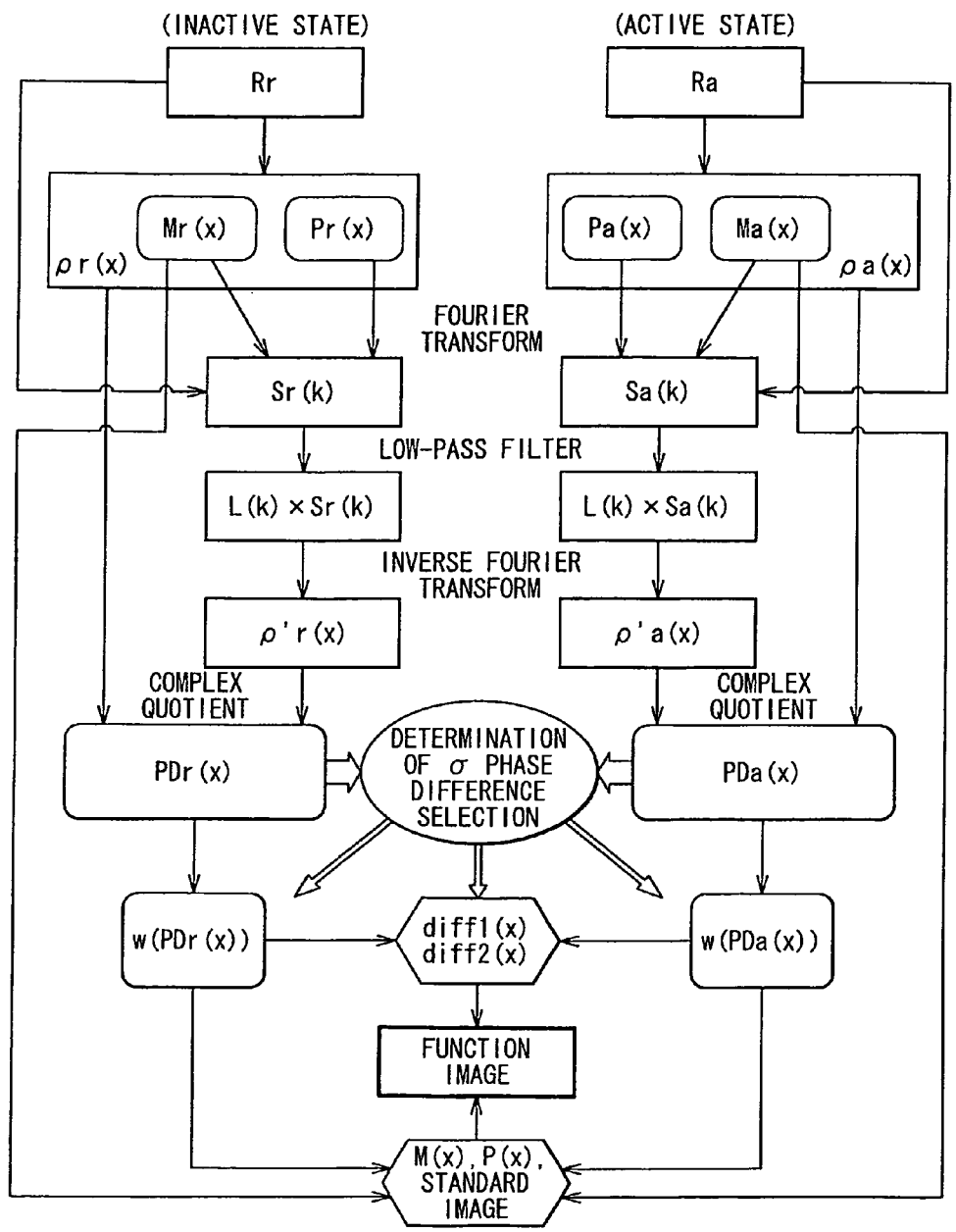
FIG. 5 is a flowchart illustrating data flow through creation of a function image with an activated region rendered in an MRI apparatus according to a second embodiment of the invention.

FIG. 5 illustrates data flow through creation of the function image with an activated region rendered. The operation section 26A starts operation in response to an instruction from a user. The operation section 26A first outputs a control signal requesting a sequence controller 25 to acquire raw data in each of the active and inactive states using a predetermined pulse sequence. Thus, the sequence controller 25 outputs, in each of the active and inactive states, a control signal in accordance with the predetermined pulse sequence to each of a gradient-magnetic-field source 22, a transmission section 23, and a reception section 24. Each of the gradient-magnetic-field source 22 and the transmission section 23 outputs a predetermined current pulse to a coil system 10 in response to the outputted control signal, and the RF coil section 13 detects an MR signal. The detected MR signal is converted into raw data Rr or Ra by the reception section 24. The obtained raw data Rr or Ra are inputted from the reception section 24 to the sequence controller 25, and then the controller 25 transfers (inputs) the raw data to the operation section 26A. In this way, the operation section 26A acquires data (raw data Rr or Ra) corresponding to the MR signal in each of the active and inactive states. The suffix r of Rr means inaction, and the suffix a of Ra means action. A suffix r or a has the same meaning below.

The raw data in each of the active and inactive states are acquired at certain intervals. Accordingly, the operation section 26A may take a method other than the above method where a single control signal is outputted to perform a pulse sequence in each of the active and inactive states. For example, the operation section 26A may output a control signal one time in each of the active and inactive states so that the sequence controller 25 is allowed to perform a pulse sequence whenever the control signal is outputted.

In the following data processing, the operation section 26A may acquire raw data in both the active and inactive states, and then collectively process the acquired raw data in both the states to derive the enhancement function described below. Alternatively, the operation section 26A may process first acquired raw data to derive an enhancement function in the inactive state, and then process second acquired raw data to derive an enhancement function in the active state. In the following, description is made on a case where raw data in both the active and inactive states are acquired, and then the acquired raw data in both the states are collectively processed.

(Creation of Magnitude Image M(x) and Phase Image P(x))

Next, the operation section 26A disposes, in a k space set in an internal memory (not shown), the raw data Rr and Ra in the respective active and inactive states inputted from the sequence controller 25. The operation section 26A performs inverse Fourier transform of the k-space data Sr(k) and Sa(k) disposed in the k space to reconstruct an image. Such reconstruction provides a complex image ρr(x) (third complex image) and a complex image ρa(x) (fourth complex image), each having a real image in a real part and an imaginary image in an imaginary part. The operation section 26A obtains a magnitude image Mr(x) and a phase image Pr(x) from the complex image ρr(x). Furthermore, the operation section 26A obtains a magnitude image Ma(x) and a phase image Pa(x) from the complex image ρa(x).

(Creation of Phase Difference Images PDr(x) and PDa(x))

Next, the operation section 26A performs processing to extract phase difference while removing phase wrapping. Specifically, the operation section 26A first performs Fourier transform of the complex images ρr(x) and ρa(x) to temporarily return the complex images ρr(x) and ρa(x) to the k-space data Sr(k) and Sa(k), respectively. Alternatively, the operation section 26A reads the k-space data Sr(k) and Sa(k) that have been disposed in the k space. Next, the operation section 26A filters the Sr(k) and Sa(k) with LPF and performs inverse Fourier transform of data L(k)*Sr(k) and L(k)*Sa(k) obtained thereby, and thus obtains a complex image ρ'r(x) (fifth complex image) and a complex image ρ'a(x) (sixth complex image).

Next, the operation section 26A creates a phase difference image PDr(x) (first phase difference image) in the inactive state and a phase difference image PDa(x) (second phase difference image) in the active state using the complex images ρr(x) and ρa(x) and the complex images ρ'r(x) and ρ'a(x). Specifically, the operation section 26A divides the complex images ρr(x) and ρa(x) by the complex images ρ'r(x) and ρ'a(x), respectively, as operation of complex quotients, and thus creates the phase difference images PDr(x) and PDa(x). This allows phase wrapping in a phase portion to be removed. Here, phase difference included in each of the phase difference images PDr(x) and PDa(x) has a width of 2π. In the embodiment, phase difference in the PDr(x) and phase difference in the PDa(x) are assumed to be −π≤PDr(x)<π and $-\pi \leq PDa(x) < \pi$, respectively. A sign of phase difference in each of the PDr(x) and the PDa(x) is determined by $-\gamma^*\Delta B^*TE$, and defined to be negative particularly for venous blood. However, even if a level of phase difference is not changed, the sign of phase difference in the phase difference image PDr(x) or PDa(x) may be changed by changing definition of LPF and definition of the complex quotient in extraction of each of the phase difference images PDr(x) and PDa(x). To cope with this, the definitions are made such that the sign is negative particularly for venous blood.

(Creation of Function Signal Image Diff1(x) or Function Signal Image Diff2(x))

Next, the operation section 26A enhances phase difference variation (PDr(x)−PDa(x)) between the phase difference images, or produces a difference between respective enhanced images of the phase difference images PDr(x) and PDa(x). Each of the phase difference images PDr(x) and PDa(x) includes a phase caused by a function of a tissue itself, as well as a phase caused by unique response of a tissue to a static magnetic field (susceptibility of the tissue). Thus, the difference (PDr(x)−PDa(x)) between the phase difference images is obtained, or the difference between the respective enhanced images of the phase difference images PDr(x) and PDa(x) is obtained, thereby the phase caused by unique response of a tissue (susceptibility of the tissue) is removed, and consequently a phase added by action of the tissue or a phase corresponding to the added phase is extracted.

Specifically, first, the operation section 26A obtains the difference between the phase difference images PDr(x) and PDa(x) and thus produces the phase difference variation (PDr(x)−PDa(x)). Next, the operation section 26A selects an exponential function (first exponential function) as an enhancement function w(θ) for enhancing the phase difference variation (PDr(x)−PDa(x)) between the phase difference images. Then, the operation section 26A enhances the phase difference variation (PDr(x)−PDa(x)) with the enhancement function w(θ), and thus obtains an enhanced image w(PDr(x)−PDa(x)). Consequently, a function signal image diff1(x) (first function signal image) enhanced in phase difference variation is obtained.

Furthermore, the operation section 26A selects an exponential function (second exponential function) as an enhancement function w(θ) for enhancing the phase difference image PDr(x) and the phase difference image PDa(x). Then, the operation section 26A enhances the phase difference image PDr(x) and the phase difference image PDa(x) with the enhancement function w(θ), and thus obtains enhanced images w(PDr(x)) and w(PDa(x)). Next, the operation section 26A obtains a difference between the enhanced images w(PDr(x)) and w(PDa(x)). This provides a function signal image diff2(x) (second function signal image) as a difference between the enhanced images enhanced in phase difference.

diff1(x)=w(PDr(x)−PDa(x))

diff2(x)=w(PDr(x))−w(PDa(x))

Here, an exponential function is used as the enhancement function w(θ). In the embodiment, a π function is used as an example of the exponential function. The π function is expressed by the two expressions in the above embodiment.

(Determination of a, b, and σ)

Any of the parameters a, b, and σ has a value of a real number. The respective parameters a and b are determined depending on filter size of LPF. Furthermore, the respective parameters a and b are determined to maximize contrast C between an objective tissue and a background thereof or a contrast-to-noise ratio CNR. The parameter σ is determined, for example, by a standard deviation of tissues each having a mean phase value of approximately 0 (zero) on the phase difference image PDr(x) or PDa(x). However, in some cases, any of tissues on any of phase difference images PDr(x) or PDa(x) captured at the same time does not have a mean phase value of approximately 0 (zero). In such a case, the parameter σ is determined, for example, based on the contrast C or the contrast-to-noise ratio CNR. The contrast C and the contrast-to-noise ratio CNR are determined in the same way as in the above embodiment.

In some cases, the diff1 or diff2 includes noise that is hardly removed even if the π function is used as the enhancement function w(θ). When such noise is included, a threshold value for distinguishing the noise from a signal is preferably set to remove the noise. When the threshold value is set, the operation section 26A removes a signal equal to or lower than the threshold value (or signal lower than the threshold value) in the function signal image diff1(x) or diff2(x), as necessary. The threshold value is preferably beforehand set based on an experimental result. However, in some cases, the threshold value is preferably appropriately reset in correspondence to changed filter size or the like. The threshold value may be changed by the operation section 26A automatically in accordance with predetermined algorithm or may be changed manually by a user of an MRI apparatus.

(Creation of Function Image I'(x) with Activated Region Rendered)

Next, the operation section 26A masks a predetermined image with the function signal image diff1(x) or diff2(x), thereby creating a function image I'(x) (first function image or second function image) with activated region rendered. Here, the predetermined image to be masked includes, for example, a magnitude image Mr(x), a magnitude image Ma(x), a standard image, or a morphological image I(x) beforehand created by PADRE as described in the above embodiment. Here, the morphological image I(x) may be created using imaging data in the inactive state or created using imaging data in the active state. In this way, the function image I'(x) with activated region rendered is created. When an imaging region includes a brain, a standard brain image may be used as the standard image.

(Medical Meaning Provided from Function Image I'(x))

It is believed that attention is usefully focused on predetermined data among data obtained during creation of the function image I'(x) to analyze medical meaning of the function image I'(x). Specifically, the operation section 26A focuses on a sign of each of the three data PDr(x), diff1(x), and diff2(x), and determines a case corresponding to each of the three data between the following cases I, II, III, and IV.

$PDr(x) \geq 0, \text{diff1}(x) > 0, \text{diff2}(x) > 0$      I:

$PDr(x) \geq 0, \text{diff1}(x) < 0, \text{diff2}(x) < 0$      II:

$PDr(x) < 0, \text{diff1}(x) > 0, \text{diff2}(x) > 0$      III:

$PDr(x) < 0, \text{diff1}(x) < 0, \text{diff2}(x) < 0$      IV:

Considering that change in tissue function is mainly indicated by change in oxygen amount in blood, when the phase difference image PDr(x) has a negative value in the inactive state, blood is regarded to be mainly venous blood. Conversely, when the phase difference image PDr(x) has a positive value in the inactive state, blood is regarded to be mainly arterial blood. Those suggest that in the case that the phase difference image PDr(x) is negative, change of a vein may be observed with the vein as a target. Those further suggest that in the case that the phase difference image PDr(x) is positive, change of an artery may be observed with the artery as a target.

It is conceivable that in the case that the function signal image diff1(x) or diff2(x) moves positively, the case corresponds to a case of increased oxygen level in the blood. In contrast, it is conceivable that in the case that the function signal image diff1(x) or diff2(x) moves negatively, the case corresponds to a case of decreased oxygen level in the blood. In other words, it is conceivable that when a tissue is activated by action and thus consumes much oxygen, the function signal image diff1(x) or diff2(x) necessarily changes negatively. However, even in the case that the function signal image diff1(x) or diff2(x) necessarily changes positively, such change may be considered to be associated with action. This is conceivably corresponding to a case that oxygen amount in an artery increases since a tissue needs much oxygen due to action.

When the above cases are roughly classified in accordance with such consideration, the following cases are likely to be given. This enables that the operation section 26A allows the display section 26C to display a case corresponding to the function image I'(x) between cases of I, II, III, and IV so that a user is provided with reference information for analyzing medical meaning of the function image I'(x) by the user. Since the above consideration needs a view with more complicated tissue action as a background, the function image I'(x) is believed to have a larger amount of information in practice.

I: mainly a case where a large amount of oxygen is supplied to an artery

II: mainly a case where a decreased amount of oxygen is supplied to an artery

III: mainly a case where an extremely large amount of oxygen is supplied, and unconsumed oxygen comes into a vein IV: mainly a case where a larger amount of oxygen in a vein is consumed due to tissue action Next, an advantage of the MRI apparatus of the embodiment is described.

In the embodiment, a phase difference image PDr(x) is created using a complex image σr(x), including a magnitude image Mr(x) and a phase image Pr(x), created from an MR signal in the inactive state, and a complex image σ'r(x) obtained through filtering the complex image σr(x). In addition, a phase difference image PDa(x) is created using a complex image σa(x), including a magnitude image Ma(x) and a phase image Pa(x), created from an MR signal in the active state, and a complex image σ'a(x) obtained through filtering the complex image σa(x). In addition, function signal images diff1(x) and diff2(x) are created using the phase difference images PDr(x) and PDa(x). Furthermore, the magnitude image Mr(x), the magnitude image Ma(x), the standard image, or the morphological image I(x) is masked with the function signal image diff1(x) or diff2(x), so that a function image I'(x) with activated region rendered is created.

In this way, in the embodiment, the function signal image diff1(x) or diff2(x) created from the phase difference image PDr(x) in the inactive state and the phase difference image PDa(x) in the active state is selected for enhancing phase difference. This makes it possible to reflect the BOLD effect induced by an activated tissue, and besides to distinguish a signal caused by entering of blood flow (for example, a signal due to a two-dimensional effect caused by activation of a tissue in a large blood vessel other than a capillary vessel). As a result, an activated region is shown mainly in a cortex portion, allowing accurate display of the activated region even from an anatomical standpoint. In addition, an exponential function is selected as the enhancement function in the embodiment. This, for example, makes it possible to approximate an optional power function with optional accuracy, enabling flexible response to change in distribution of phase difference.

In a previous imaging method of a brain function using only a magnitude signal, since local change in magnetic field is extracted as $T_2^*$ contrast using the BOLD effect, change in signal due to simple function activation has been hardly distinguished from that due to entering of blood flow. However, in the embodiment, those may be clearly distinguished from each other by using the enhancement function.

In addition, in the previous method, the magnitude signal is used and therefore signal change is not sensitive to spatial change across pixels. This inevitably reduces the number of pixels, and therefore an indicating region becomes large, leading to ambiguity. This is greatly due to statistical result presentation sequentially including multiple times of activation, statistical processing, and presentation of a function signal region. As a result, for example, for a small area such as a gustatory area, while activation itself may be indicated, a detailed activated portion has been hard to be indicated.

In the embodiment, since the phase images Pr(x) and Pa(x) are used, a signal may be captured with high resolution due to high sensitivity of the phase image to magnetic response of a tissue. For example, while 64*64 matrix has been normally used in the previous method, 256*256 matrix or 512*512 matrix may be achieved in the embodiment. Accordingly, the activated region may be indicated in a pinpoint manner in the embodiment. Accordingly, spatial resolution may be improved to, for example, 1 mm or less, and therefore an activated site may be accurately indicated even in a small activated region.

Moreover, in the previous method, statistical processing is performed to remove influence of a low signal and influence of various kinds of noise, so that a signal is determined. To perform the statistical processing, multiple times (typically, 10 to 15 times) of activation needs to be performed for adding signals. This causes heavy load on a subject. Moreover, in the case that signal saturation occurs after several times of activation, statistical processing may conversely cause reduction in reliability. A signal presented by a statistical result indicates distribution of a highly reliable portion of a function signal, resulting in display of a region having a certain size. It is therefore difficult to indicate an activated region in a pinpoint manner.

In the embodiment, since the phase images Pr(x) and Pa(x) are used, a signal may be determined by one-time activation in principle based on high spatial-resolution of a phase. This is because phase noise signals having positive and negative, random values are canceled by one another over cumulative time, and therefore phase noise is reduced, leading to improvement in SNR of a phase difference signal. A theoretical background of this is the ergodic theory on time average and frequency average, and therefore it is believed that statistical operation may be replaced by time average. This makes it possible to create a function image that is statistically synonymous with that in the previous method.

In addition, since the embodiment uses enhancement technique with PADRE as a principle, change in oxygen concentration in a tissue before and after activation, which has been hardly provided from a function image in the past, may be measured based on flexible phase difference selection. In addition, the embodiment makes it possible to capture an aspect that a tissue itself is activated and consumes oxygen. Such change in a tissue has been hardly captured in the previous method. Even in this regard, the enhancement technique of the embodiment is remarkably successful.

Modification of each of Embodiments

While the invention has been described with a plurality of embodiments, the invention is not limited to those, and various modifications or alterations of the invention may be made.

For example, each of the embodiments may be designed in such a manner that the same magnitude images M(x) and the same phase images P(x) are subjected to LPF processing in the k space with two kinds of filter size different from each other, and thus two function signal images (diff3(x) and diff4(x)) are obtained, and a difference (diff3(x)−diff4(x)) between the two function signal images is obtained, and the magnitude image Mr(x), the magnitude image Ma(x), the standard image, or the morphological image I(x) is masked with the difference. This makes it possible to remove or extract only a signal having a value on a tissue having a certain size.

In particular, when the function signal image diff3(x) is obtained through LPF processing with a small filter size, and the function signal image diff4(x) is obtained through LPF processing with a large filter size, aliasing (signal that is not regarded to have a value associated with original tissue activation), associated with change in blood flowing into a blood vessel having a size large enough to be displayed on an image, may be removed or extracted.

While description is made such that operation is made to an image itself throughout the description, operation is made to a signal for each of pixels of the image in actual calculation. For example, when an enhanced image w(PD(x)) is multiplied by a magnitude image M(x), a signal for each of pixels of the enhanced image w(PD(x)) is multiplied by a signal for each of pixels of the magnitude image M(x).

What is claimed is:

1. A phase difference enhanced imaging method comprising:
   a first step of creating a phase difference image using a first complex image including a magnitude image and a phase image obtained from a magnetic resonance signal and a second complex image obtained by filtering the first complex image;
   a second step of creating an enhanced image through selecting a phase corresponding to an objective tissue in the phase difference image taking account of change in distribution of phase difference due to the filtering, and selecting an exponential function as an enhancement function for enhancing the selected phase, and enhancing the selected phase by the exponential function; and
   a third step of creating a phase difference enhanced image by masking a predetermined image with the enhanced image.

2. The phase difference enhanced imaging method according to claim 1, wherein a π function is selected as the exponential function in the second step.

3. The phase difference enhanced imaging method according to claim 2, wherein the π function is expressed by the following expressions; and
   wherein θ is a phase angle corresponding to an objective tissue:

$w(\theta)=1 \ldots (-\sigma \leq v \leq \sigma)$ $w(\theta)=\exp(-a*(Abs(\theta)-\sigma)^b) \ldots$ (θ is out of the above rage)

w(θ): enhancement function
   a, b, σ: parameter, having a value of a real number
   Abs(θ): absolute value of θ.

4. The phase difference enhanced imaging method according to claim 3, wherein the parameters a and b are each determined based on filter size and contrast or a contrast-to-noise ratio.

5. The phase difference enhanced imaging method according to claim 3, wherein the parameter σ is determined based on the phase difference image in the second step.

6. The phase difference enhanced imaging method according to claim 1, wherein the phase difference image is created by dividing the first complex image by the second complex image in the first step.

7. The phase difference enhanced imaging method according to claim 1, wherein the magnetic resonance signal is obtained by a gradient echo pulse sequence.

8. The phase difference enhanced imaging method according to claim 1, wherein the predetermined image corresponds to the magnitude image.

9. The phase difference enhanced imaging method according to claim 1,
   wherein in the first step, the magnetic resonance signal is detected, for each of channels, from a plurality of channels disposed in parallel around a subject, and the phase difference image is created for each of the channels,
   in the second step, an exponential function is selected as an enhancement function corresponding to the phase difference image for each of the channels, and the selected phase is enhanced by the exponential function, thereby an enhanced image is created for each of the channels, and
   in the third step, a predetermined image is masked with the enhanced image for each of the channels, thereby a phase difference enhanced image is created for each of the channels, and an arithmetic mean or a weighted mean of phase difference enhanced images for the respective channels is created.

10. A functional image creating method comprising:
    a first step of creating a third complex image, including a magnitude image and a phase image, from a magnetic resonance signal in an inactive state of an objective tissue, and creating a fourth complex image, including a magnitude image and a phase image, from a magnetic resonance signal in an active state of the objective tissue;
    a second step of creating a fifth complex image by filtering the third complex image and creating a sixth complex image by filtering the fourth complex image, and then creating a first phase difference image using the third complex image and the fifth complex image and creating a second phase difference image using the fourth complex image and the sixth complex image;
    a third step of creating a first function signal image through creating phase difference variation by obtaining a difference between the first phase difference image and the second phase difference image, and then selecting a first exponential function as an enhancement function for enhancing the phase difference variation, and enhancing the phase difference variation by the first exponential function; and
    a fourth step of creating a first function image with an activated region rendered by masking a predetermined image with the first function signal image.

11. The functional image creating method according to claim 10, wherein a signal equal to or lower than a threshold value included in the first function signal image is removed in the third step.

12. The functional image creating method according to claim 10,
wherein the predetermined image includes the magnitude image, a standard image, or a phase difference enhanced image beforehand created through the following fifth to seventh steps, fifth step: creating a third phase difference image using a seventh complex image including a magnitude image and a phase image obtained from a magnetic resonance signal and an eighth complex image obtained by filtering the seventh complex image, sixth step: creating a third enhanced image through selecting a phase corresponding to an objective tissue in the third phase difference image taking account of change in distribution of phase difference due to the filtering, and selecting a third exponential function as an enhancement function for enhancing the selected phase, and enhancing the selected phase by the third exponential function; and seventh step: creating the phase difference enhanced image by masking a predetermined image with the third enhanced image.

13. A functional image creating method comprising:
a first step of creating a third complex image, including a magnitude image and a phase image, from a magnetic resonance signal in an inactive state of an objective tissue, and creating a fourth complex image, including a magnitude image and a phase image, from a magnetic resonance signal in an active state of the objective tissue;

a second step of creating a fifth complex image by filtering the third complex image and creating a sixth complex image by filtering the fourth complex image, and then creating a first phase difference image using the third complex image and the fifth complex image and creating a second phase difference image using the fourth complex image and the sixth complex image;

a third step of creating a second function signal image through selecting a second exponential function as an enhancement function for enhancing the first phase difference image and the second phase difference image, creating a first enhanced image and a second enhanced image by enhancing the first phase difference image and the second phase difference image by the second exponential function, respectively, and obtaining a difference between the first enhanced image and the second enhanced image; and a fourth step of creating a second function image with an activated region rendered by masking a predetermined image with the second function signal image.

14. The functional image creating method according to claim 13,
wherein the predetermined image includes the magnitude image, a standard image, or a phase difference enhanced image beforehand created through the following fifth to seventh steps, fifth step: creating a third phase difference image using a seventh complex image including a magnitude image and a phase image obtained from a magnetic resonance signal and an eighth complex image obtained by filtering the seventh complex image, sixth step: creating a third enhanced image through selecting a phase corresponding to an objective tissue in the third phase difference image taking account of change in distribution of phase difference due to the filtering, and selecting a third exponential function as an enhancement function for enhancing the selected phase, and enhancing the selected phase by the third exponential function; and seventh step: creating the phase difference enhanced image by masking a predetermined image with the third enhanced image.

15. The functional image creating method according to claim 13, wherein a signal equal to or lower than a threshold value included in the second function signal image is removed in the third step.

16. The functional image creating method according to claim 13,
wherein in the third step, phase difference variation is created by obtaining a difference between the first phase difference image and the second phase difference image, and then a first exponential function is selected as an enhancement function for enhancing the phase difference variation, and the phase difference variation is enhanced by the first exponential function, and thereby a first function signal image is created, and
in the fourth step, a predetermined image is masked with the first function signal image, and thereby a first function image with an activated region rendered is created.

17. The functional image creating method according to claim 16, wherein in the fourth step, a case corresponding to each of the first phase difference image, the first function signal image, and the second function signal image is determined between the following cases I, II, III, and IV, $$PDr(x) \geq 0, \text{diff1}(x) > 0, \text{diff2}(x) > 0 \qquad \text{I:}$$

$$PDr(x) \geq 0, \text{diff1}(x) < 0, \text{diff2}(x) < 0 \qquad \text{II:}$$

$$PDr(x) < 0, \text{diff1}(x) > 0, \text{diff2}(x) > 0 \qquad \text{III:}$$

$$PDr(x) < 0, \text{diff1}(x) < 0, \text{diff2}(x) < 0 \qquad \text{IV:}$$

$PDr(x)$: the first phase difference image
$\text{diff1}(x)$: the first function signal image
$\text{diff2}(x)$: the second function signal image.

18. A non-transitory recording medium storing instructions for causing a computer to execute:
a first step of creating a phase difference image using a first complex image including a magnitude image and a phase image obtained from a magnetic resonance signal and a second complex image obtained by filtering the first complex image;

a second step of creating an enhanced image through selecting a phase corresponding to an objective tissue in the phase difference image taking account of change in distribution of phase difference due to the filtering, selecting an exponential function as an enhancement function for enhancing the selected phase, and enhancing the selected phase by the exponential function; and a third step of creating a phase difference enhanced image by masking a predetermined image with the enhanced image.

19. A phase difference enhanced imaging apparatus comprising:
a phase difference image creation section creating a phase difference image using a first complex image including a magnitude image and a phase image obtained from a magnetic resonance signal and a second complex image obtained by filtering the first complex image;

an enhanced image creation section creating an enhanced image through selecting a phase corresponding to an objective tissue in the phase difference image taking account of change in distribution of phase difference due to the filtering, selecting an exponential function as an enhancement function for enhancing the selected phase, and enhancing the selected phase by the exponential function; and a phase difference enhanced image creation section creating a phase difference enhanced image by masking a predetermined image with the enhanced image.

20. A functional image creating apparatus comprising:

a complex image creation section creating a third complex image, including a magnitude image and a phase image, from a magnetic resonance signal in an inactive state of an objective tissue, and creating a fourth complex image, including a magnitude image and a phase image, from a magnetic resonance signal in an active state of the objective tissue;

a phase difference image creation section creating a fifth complex image by filtering the third complex image and creating a sixth complex image by filtering the fourth complex image, and then creating a first phase difference image using the third complex image and the fifth complex image and creating a second phase difference image using the fourth complex image and the sixth complex image;

a function signal image creation section creating a first function signal image through creating phase difference variation by obtaining a difference between the first phase difference image and the second phase difference image, and then selecting a first exponential function as an enhancement function for enhancing the phase difference variation, and enhancing the phase difference variation by the first exponential function; and an activated region rendering section creating a first function image with an activated region rendered by masking a predetermined image with the first function signal image.

21. A functional image creating apparatus comprising:

a complex image creation section creating a third complex image, including a magnitude image and a phase image, from a magnetic resonance signal in an inactive state of an objective tissue, and creating a fourth complex image, including a magnitude image and a phase image, from a magnetic resonance signal in an active state of the objective tissue;

a phase difference image creation section creating a fifth complex image by filtering the third complex image and creating a sixth complex image by filtering the fourth complex image, and then creating a first phase difference image using the third complex image and the fifth complex image and creating a second phase difference image using the fourth complex image and the sixth complex image;

a function signal image creation section creating a second function signal image through selecting a second exponential function as an enhancement function for enhancing the first phase difference image and the second phase difference image, creating a first enhanced image and a second enhanced image by enhancing the first phase difference image and the second phase difference image by the second exponential function, respectively, and obtaining a difference between the first enhanced image and the second enhanced image; and an activated region rendering section creating a second function image with an activated region rendered by masking a predetermined image with the second function signal image.

22. A magnetic resonance imaging apparatus comprising:

a wave detector applying a static magnetic field, a gradient magnetic field, and an RF magnetic field to an object and detecting a magnetic resonance signal emitted from the object; and an image creation section creating an image based on the magnetic resonance signal detected by the wave detector, wherein the image creation section including a phase difference image creation section creating a phase difference image using a first complex image including a magnitude image and a phase image obtained from a magnetic resonance signal and a second complex image obtained by filtering the first complex image, an enhanced image creation section creating an enhanced image through selecting a phase corresponding to an objective tissue in the phase difference image taking account of change in distribution of phase difference due to the filtering, and selecting an exponential function as an enhancement function for enhancing the selected phase, and enhancing the selected phase by the exponential function, and a phase difference enhanced image creation section creating a phase difference enhanced image by masking a predetermined image with the enhanced image.

* * * * *